(12) United States Patent
Bastianelli et al.

(10) Patent No.: US 9,872,876 B2
(45) Date of Patent: *Jan. 23, 2018

(54) PHARMACEUTICAL COMPOSITION FOR USE IN THE TREATMENT AND/OR THE PREVENTION OF OSTEOARTICULAR DISEASES

(71) Applicant: BONE THERAPEUTICS, Gosselies (BE)

(72) Inventors: Enrico Bastianelli, Rhode-Saint-Genese (BE); Pierre Attali, Vincennes (FR); Chris Vervaet, Izegem (BE)

(73) Assignee: BONE THERAPEUTICS, Gosselies (BE)

( * ) Notice: Subject to any disclaimer, the term of this patent is extended or adjusted under 35 U.S.C. 154(b) by 0 days.

This patent is subject to a terminal disclaimer.

(21) Appl. No.: 15/269,216

(22) Filed: Sep. 19, 2016

(65) Prior Publication Data

US 2017/0056434 A1    Mar. 2, 2017

Related U.S. Application Data

(60) Division of application No. 13/625,601, filed on Sep. 24, 2012, now Pat. No. 9,446,065, which is a continuation of application No. 12/811,665, filed as application No. PCT/EP2009/051739 on Feb. 13, 2009, now abandoned.

(30) Foreign Application Priority Data

Feb. 15, 2008  (EP) ..................................... 08101682
Jun. 13, 2008  (EP) ..................................... 08158285

(51) Int. Cl.
| | | |
|---|---|---|
| A61K 9/00 | (2006.01) |
| A61K 31/00 | (2006.01) |
| A61K 31/728 | (2006.01) |
| A61K 31/4168 | (2006.01) |
| A61K 31/726 | (2006.01) |
| A61K 45/06 | (2006.01) |
| A61K 47/36 | (2006.01) |
| A61K 31/56 | (2006.01) |
| A61K 35/12 | (2015.01) |
| A61K 35/545 | (2015.01) |
| A61M 5/28 | (2006.01) |
| A61K 31/573 | (2006.01) |
| A61K 35/28 | (2015.01) |
| A61K 31/4164 | (2006.01) |
| A61K 31/4174 | (2006.01) |
| A61K 31/4178 | (2006.01) |

(52) U.S. Cl.
CPC .......... *A61K 31/728* (2013.01); *A61K 9/0019* (2013.01); *A61K 31/4164* (2013.01); *A61K 31/4168* (2013.01); *A61K 31/4174* (2013.01); *A61K 31/4178* (2013.01); *A61K 31/56* (2013.01); *A61K 31/573* (2013.01); *A61K 31/726* (2013.01); *A61K 35/12* (2013.01); *A61K 35/28* (2013.01); *A61K 35/545* (2013.01); *A61K 45/06* (2013.01); *A61K 47/36* (2013.01); *A61M 5/283* (2013.01)

(58) Field of Classification Search
CPC .... A61K 45/06; A61K 9/0019; A61K 31/726; A61K 31/4168; A61K 31/728
See application file for complete search history.

(56) References Cited

U.S. PATENT DOCUMENTS

| | | | |
|---|---|---|---|
| 6,214,369 B1 * | 4/2001 | Grande | A61F 2/30756 424/423 |
| 6,248,345 B1 * | 6/2001 | Goldenheim | A61K 9/0019 424/426 |
| 6,331,311 B1 | 12/2001 | Brodbeck et al. | |
| 6,387,413 B1 | 5/2002 | Miyata et al. | |
| 6,503,504 B1 | 1/2003 | Vandenburgh | |
| 6,641,834 B2 * | 11/2003 | Olejnik | A61K 9/0048 424/400 |
| 2002/0005205 A1 * | 1/2002 | Barry | C12N 5/0663 128/898 |
| 2003/0022926 A1 * | 1/2003 | Lavand'Homme | A61K 31/00 514/388 |
| 2006/0194805 A1 | 8/2006 | Bakthavatchalam et al. | |
| 2007/0042951 A1 | 2/2007 | Olejnik et al. | |
| 2007/0225217 A1 | 9/2007 | Chappell et al. | |

FOREIGN PATENT DOCUMENTS

| | | |
|---|---|---|
| WO | 00/17326 A1 | 3/2000 |
| WO | 01/80865 A1 | 11/2001 |
| WO | 2005/039567 A1 | 5/2005 |
| WO | 2006/039704 A2 | 4/2006 |
| WO | 2006/092619 A1 | 9/2006 |

OTHER PUBLICATIONS

Gentili et al. Peripheral analgesic effect of intra-articular clonidine. Pain 64 (1996):593-596.*
Gentili et al. Peripheral analgesic effect of intra-articular clonidine. Pain, 64 (1996) 593-596.

\* cited by examiner

*Primary Examiner* — Robert A Wax
*Assistant Examiner* — Olga V Tcherkasskaya
(74) *Attorney, Agent, or Firm* — Merchant & Gould P.C.

(57) ABSTRACT

An intra-articular pharmaceutical composition is used for the treatment and/or the prevention of acute or chronic osteoarticular diseases and acute or chronic osteoarticular symptoms especially osteoarthritis. The composition includes a possibly adequate pharmaceutical carrier or diluent, a glycosaminoglycan, a compound activating the alpha 2 adrenergic receptor, an anti-inflammatory agent and stem cells.

9 Claims, 3 Drawing Sheets

PHARMACEUTICAL COMPOSITION FOR USE IN THE TREATMENT AND/OR THE PREVENTION OF OSTEOARTICULAR DISEASES

This application is a Divisional of Ser. No. 13/625,601 filed 24 Sep. 2012, which is a Continuation of Ser. No. 12/811,665 filed 2 Jul. 2010 which is a National Stage Application of PCT/EP2009/051739, filed 13 Feb. 2009, which claims benefit of Serial No. 08158285.0, filed 13 Jun. 2008 in Europe and Serial No. 08101682.6, filed 15 Feb. 2008 in Europe, and which applications are incorporated herein by reference. To the extent appropriate, a claim of priority is made to each of the above disclosed applications.

FIELD OF THE INVENTION

The present invention is in the pharmaceutical field and is related to a new pharmaceutical composition for use in the treatment and/or the prevention of acute and/or chronic osteoarticular diseases.

BACKGROUND OF THE INVENTION

Osteoarthritis, the most common form, of arthritis, is a disease characterised by a slow degenerative processes in the articular cartilage, subchondral bone associated with marginal osteophyte formation, and low grade inflammation. Osteoarthritis is believed to affect 15% of the population in its chronic form. Of those, one-quarter are severely disabled. Most cases of osteoarthritis have no known cause and are referred to as primary osteoarthritis. When the cause of the osteoarthritis is known, the condition is referred to as secondary osteoarthritis. Secondary osteoarthritis is caused by another disease or condition. Conditions that can lead to secondary osteoarthritis include repeated trauma or surgery to the joint structures, abnormal joints at birth (congenital abnormalities), gout, diabetes, and other hormone disorders. Other forms of arthritis are systemic illnesses, such as rheumatoid arthritis and systemic lupus erythematosus (SLE).

Osteoarthritis involves mainly the hips, knees, spine, and the interphalangeal joints. The most common symptom of osteoarthritis is pain in the affected joint(s) after repetitive use. Joint pain is usually worse later in the day. There can be swelling, warmth, and creaking of the affected joints. Pain and stiffness of the joints can also occur after long periods of inactivity. In severe osteoarthritis, complete loss of cartilage cushion causes friction between bones, causing pain at rest or pain with limited motion.

Osteoarthritis is characterized by a slow degradation of cartilage over several years. In normal cartilage, a delicate balance exists between matrix synthesis and degradation; in osteoarthritis, however, cartilage degradation exceeds synthesis. The balance between synthesis and degradation is affected by age and is regulated by several factors produced by the synovium and chondrocytes, including cytokines, growth factors, aggrecanases, and matrix metalloproteinases In addition to water, the extracellular matrix is composed of proteoglycans, made up of glycosaminoglycans attached to a backbone made of hyaluronic acid, entrapped within a collagenous framework or fibrillary matrix. A significant proteoglycal in articular cartilage is aggrecan, which binds to hyaluronic acid and helps provide the compressibility and elasticity of cartilage. Aggrecan is cleaved by aggrecanases, leading to its degradation and to subsequent erosion of cartilage. The loss of aggrecan from the cartilage matrix is one of the first pathophysiological changes observed in OA.

Cytokines produced by the synovium and chondrocytes, especially IL-1beta and Tumor Necrosis Factor alpha (TNF-alpha), are also key players in the degradation of cartilage. IL-1beta is spontaneously released from cartilage of osteoarthritis but not normal cartilage. Both IL-1beta and TNF-alpha stimulate their own production and the production of other cytokines (e.g., IL-8, IL-6, and leukotriene inhibitory factor), proteases, and prostaglandin $E_2$ ($PGE_2$). Synthesis of the inflammatory cytokines IL-1beta and TNF-alpha and expression of their receptors are enhanced in osteoarthritis. Both cytokines have been shown to potently induce degradation of cartilage in vitro. Other proinflammatory cytokines overexpressed in osteoarthritis include IL-6, IL-8, IL-11, and IL-17, as well as leukotriene inhibitory factor.

The extracellular matrix (ECM) composing the cartilage is degraded by locally produced matrix metalloproteinases. Proinflammatory cytokines, including IL-1beta; TNF-alpha, IL-17, and IL-18, increase synthesis of matrix metalloproteinases, decrease matrix metalloproteinase enzyme inhibitors, and decrease extracellular matrix synthesis.

In an attempt to reverse the breakdown of the extracellular matrix, chondrocytes increase synthesis of matrix components including proteoglycans. Even though this activity increases, a net loss of proteoglycans in the upper cartilage layer is seen. Elevated anti-inflammatory cytokines found in the synovial fluid of osteoarthritis include IL-4, IL-10, and IL-13. Their role is to reduce production of IL-1beta, TNF-alpha, and matrix metalloproteinases, and inhibit prostaglandin release. Local production of growth and differentiation factors such as insulin-like growth factor 1, transforming growth factors, fibroblastic growth factors, and bone morphogenetic proteins also stimulate matrix synthesis.

STATE OF THE ART

Currently available pharmacological therapies target palliation of pain and include analgesics (i.e. acetaminophen, cyclooxygenase-2-specific inhibitors, non-selective non-steroidal anti-inflammatory drugs, tramadol, opioids). However, the clinical presentation of osteoarthritis is usually monoarticular or oligoarticular with fluctuations in intensity and localisation over time. It is therefore logical to consider local therapeutic modalities in order to avoid untoward systemic effects. Several compounds have been used intra-articularly (e.g., glucocorticoids, hyaluronic acid) or topically (e.g., capsaicin, methylsalicylate). However, for example, the benefit of intra-articular glucocorticoids lasts only a few days (Barron, M. C, 2007, J. M. Osteopath., 107, ES21-27).

Polysaccharides form a class of materials whose recognition of the potential utility is growing. Apart from their biological activity, one of the most important properties of polysaccharides in general is their ability to form hydrogels. Hydrogel formation can occur by a number of mechanisms and is strongly influenced by the types of monosaccharide involved, as well as the presence and nature of substituent groups. Polysaccharide gel formation is generally of two types: hydrogen bonded and ionic. Hydrogen-bonded gels are typical of molecules such as agarose (thermal gellation) and chitosan (pH-dependent gellation), whereas ionically bonded gels are characteristic of alginates and carrageenans.

Proteoglycans are one of the major macromolecules found in articular cartilage. These molecules consist of a core protein and covalently attached glycosaminoglycans (GAG) chains. The GAGs are long, unbranched heteropolysaccharides, consisting of repeated disaccharide units, with the general structure: Muronic acid amino sugar. The cartilage-specific GAGs include chondroitin 4-sulfate (glucuronic acid and N-acetyl-galactosamine with an $SO_4$ on the 4-carbon position), chondroitin 6-sulfate (glucuronic acid and N-acetyl-galactosamine with an $SO_4$ on the 6-carbon position) and keratan sulfate (galactose and N-acetyl-glucosamine with an $SO_4$ on the 6-carbon position).

These molecules are capable of forming hydrogel complexes with oppositely charged ionic polymers, particularly the cationic polysaccharide chitosan. This interaction may form the basis of a new materials approach to cartilage tissue engineering. The other important cartilage GAG is hyaluronic acid (glucuronic acid and N-acetyl-glucosamine). This molecule is one of the major components in synovial fluid. Hyaluronic acid molecules are also present in cartilage matrix as the backbone structure in proteoglycan aggregates. In general, hyaluronic acid plays a major role as an organizer of the extracellular matrix. Purified hyaluronic acid is employed as a structural biomaterial because of its high molecular weight and gel forming ability. The properties of the molecule may be broadly altered by chemical modification. For example, partial esterification of the carboxyl groups reduces the water solubility of the polymer and increases its viscosity. Extensive esterification generates materials that form water-insoluble films or swellable gels. Ethyl and benzyl esterified hyaluronate membranes have excellent healing responses and biodegradability properties. The fully esterified membranes have in vivo lifetimes of several months, whereas the partially esterified forms have been shown to degrade within a few weeks.

Hyaluronic acid is responsible for the viscoelastic quality of synovial fluid that acts as both a lubricant and shock absorber. In synovial fluid, hyaluronic acid coats the surface of the articular cartilage and shares space deeper in the cartilage among collagen fibrils and sulfated proteoglycans. It protects the cartilage and blocks the loss of proteoglycans from the cartilage matrix into the synovial space, maintaining the normal cartilage matrix. In synovial fluid from knee joints in osteoarthritis, concentrations of hyaluronic acid, glycosaminoglycans, and keratan sulfate are lower than in synovial fluid from normal knee joints. Additionally, experiments using rabbit synovial cells showed that the proinflammatory cytokines IL-1beta and TNF-alpha stimulate the expression of hyaluronic acid synthetase, which may contribute to the fragmentation of hyaluronic acid under inflammatory conditions. Exogenous hyaluronic acid may facilitate the production of newly synthesized hyaluronic acid. Hyaluronic acid and derivatives have been used as therapeutic aids in the treatment of osteoarthritis as a means of improving lubrication of articulating surfaces and thus reducing joint pain. Several in vitro culture studies have also demonstrated that hyaluronic acid has a beneficial effect by inhibiting chondrocytic chondrolysis mediated by fibronectin fragment. Hyaluronic acid has also been shown to have anti-inflammatory effects, as well as inhibitory effects on prostaglandin synthesis, and proteoglycan release and degradation.

Chitosan, a partially de-acetylated derivative of chitin, found in arthropod exoskeletons is another proteoglycan, a linear polysaccharide consisting of beta (1-4) linked D-glucosamine residues with a variable number of randomly located N-acetyl-glucosamine groups. It thus shares some characteristics with various GAGs and hyaluronic acid present in articular cartilage. Depending on the source and preparation procedure, chitosan's average molecular weight may range from about 50 to about 1000 kDa. Commercially available preparations have degrees of deacetylation ranging from about 50 to about 90%. Chitosan is a semi-crystalline polymer and the degree of crystallinity is a function of the degree of deacetylation. Crystallinity is maximum for both chitin (i.e. 0% deacetylated) and fully deacetylated (i.e. 100%) chitosan. Minimum crystallinity is achieved at intermediate degrees of deacetylation.

Much of the potential of chitosan as a biomaterial stems from its cationic nature and high charge density. The charge density allows chitosan to form insoluble ionic complexes or complex coacervates with a wide variety of water-soluble anionic polymers.

In fact, chitosan oligosaccharides have been shown to have a stimulatory effect on macrophages, and the effect has been linked to the acetylated residues. Furthermore, both chitosan and its parent molecule, chitin, have been shown to exert chemoattractive effects on neutrophils in vitro and in vivo. In vivo, chitosan is degraded by enzymatic hydrolysis. The mechanical properties of chitosan scaffolds are mainly dependent on the pore sizes and pore orientations.

Hyaluronic acid, a glycosaminoglycan, is widely used for the treatment of osteoarthritis of the knee. A survey of 2 general practices in the United Kingdom showed that about 15% of patients with osteoarthritis received intra-articular treatment with hyaluronic acid preparations. Because of its viscoelastic quality, it may replace synovial fluid. Furthermore, it may reduce the perception of pain. Beneficial molecular and cellular effects have also been reported. Hyaluronic acid is frequently applied by intra-articular injection, yet the evidence concerning its clinical relevance is conflicting. State-of-the-art systematic reviews and meta-analyses were published recently, and their authors concluded that intra-articular hyaluronic acid, at best, has a small effect; a clinically meaningful effect meaning an improvement of at least 15 mm on the visual analogue scale of pain (Bellamy et al, 2006). These data form the basis for the use of intra-articular administration of hyaluronic acid in patients with osteoarthritis. The benefits are sometimes noticed only one year after injections and, in some experiments, injections must be performed three to five-times a week (Barron, M. C, 2007).

Alpha-2-adrenergic receptor ligands especially agonists are drugs commonly used in medical practice as antihypertensive substance and in clinical anaesthesiology as component of general and locoregional anaesthesia and analgesia. They produce anxiolysis, analgesia, sedation, anaesthetic sparing effects and peri-operative hemodynamic stabilizing effects. Negative neurotoxicity studies allow their use (mainly clonidine) by systemic and perimedullar routes and for peripheral nerve blocks. Among the clinically available alpha-2-adrenoreceptors agonists, clonidine remains widely used: the substance is devoid of neurotoxicity and displays fewer side effects (i.e. hypotension and sedation) than the more potent and also more alpha-2-adrenergic receptor selective agonist, dexmedetomidine. Clonidine, a potent alpha-2-adrenergic receptors partial agonist, was used primarily for the treatment of hypertension. This drug stimulates alpha-2-adrenergic receptors in the vasomotor centres, causing a reduction of sympathetic outflow from the central nervous system. Both cardiac output and peripheral resistance are reduced resulting in a decrease in blood pressure. Higher concentrations cause a vasoconstriction by activation of postsynaptic receptors in vascular smooth muscle. However, the significant advantages of the drug are counter balanced by side effects including dryness of the mouth, sedation and dizziness. Furthermore, other activities of these compounds such as anti-inflammatory effect have never been reported by oral administration.

Besides the well-known analgesic effects of spinally administered alpha-2-adrenergic (alpha-2-adrenoceptors) agonists, their peripheral use has been commonly reported in acute pain conditions. For peri-operative analgesic techniques, clonidine is added to local anaesthetic in peritroncular nerve blocks to enhance potency and duration of analgesia. ZOUHER A et al.; 2005; Luiz-Cleber P. et al.; 2005, Murphy D R "A non-surgical approach to low back pain" Med. Health R. I., 2000). Further, intra-articular injection of clonidine and its adjunction to local anaesthetic solution for intravenous regional anaesthesia have also displayed anti-nociceptive effect (S. Armand et al 1998; Br J Anaesth. 1998; Gentili M, et al. 1996; Reuben S, et al. 1999). However, these effects are only designed to last for a few hours and not days or weeks.

Alpha-2-adrenoceptors agonists are known to block the tissue content increase of pro-inflammatory cytokines, such as TNF-alpha and IL1beta and increase the tissue content of anti-inflammatory cytokine TGF beta. This has been shown in inflammatory neuropathic pain model by partial ligation of sciatic nerve, by applying locally alpha-2-adrenergic receptor agonists by peripheral nerve block.

SUMMARY OF THE INVENTION

The invention is related to an intra-articular pharmaceutical composition for use in the treatment and/or the prevention of acute or chronic osteoarticular diseases and acute or chronic osteoarticular symptoms, especially osteoarthritis, this composition comprising
  possibly an adequate pharmaceutical carrier or diluent
  a glycosaminoglycan
  a compound activating the alpha-2-adrenergic receptor agent (compound), (different from alpha 2 agonist) preferably selected from the group consisting of a steroidal anti-inflammatory compound (such as prednisolone, dexamethasone, betamethasone, triamcinolone . . . ), a non-steroidal anti-inflammatory compound (such as ibuprofen, diclofenac, naproxen, etc.), a disease modifying antirheumatic drug (such as methotrexate, leflunoimde etc. . . . ), an anti-CD20 agent, an anti-cytokine agent (such as anti-IL1, anti-IL6, anti-IL-17), an anti-TNF agent (such as infliximab, etanercerpt, adalimumab, rituximab, etc) or a mixture thereof, and,
  possibly stem cells (differentiated or not), preferably adult human mesenchymal stem cells or (non-human) embryonic stem cells having anti-inflammatory and regenerative properties.

In the pharmaceutical composition of the invention the glycosaminoglycan is present as a film or as a matrix, preferably in the form of a paste or a gel, more preferably an hydrogel with a sufficient amount of an aqueous solvent.

Advantageously, the compound interacting with the alpha-2-adrenergic receptor is an alpha-2-adrenergic receptor agonist.

In the composition according to the invention the glycosaminoglycan and the compound activating the alpha-2-adrenergic receptor are not covalently linked or are covalently linked.

Preferably, the glycosaminoglycan is selected from the group consisting of hyaluronic acid with low (<900 kDa) or high (>900 kDa) molecular mass.

In the composition of the invention, the hyaluronic acid and the alpha 2 adrenergic receptor agonist are not covalently linked or are covalently linked.

In the composition according to the invention the glycosaminoglycan is selected from the group consisting of proteoglycan, chondroitin sulfate, keratin sulphate, hyaluronic acid (including their derivatives), chitosan, a chitosan or chitin derivative, or a mixture thereof.

The alpha-2-adrenergic receptor agonist is selected from the group consisting of clonidine, p-aminoclonidine, tiamenidine, 5-bromo-6-(2 imidazolidine-2-ylamino) quinoxaline, dexmedetomidine, detomidine, medetomidine, oxymetazonline, tizanidine, mivazerol, lofexidine, xylazine, guanfacine, guanclofine, guanoxabenz, or a derivative or structural analogue thereof, alpha-methyinorepherine, azepexole, indoramin, 6-allyl-2-5,6,7,8-tetrahydro4H-thiazolo [4,5-d]azepine diHCl.

The inventors have discovered that the pharmaceutical composition according to the invention is suitable for a treatment or prevention of acute and chronic osteoarticular diseases and associated symptoms (especially osteoarticular pain, loss of mobility or function), of inflammatory origin, such as osteoarthritis, degenerative arthritis, gonarthrosis, coxarthrosis, and other inflammatory general conditions in which joints are involved, such as autoimmune diseases, especially rheumatoid arthritis and systemic lupus erythematosus (SLE) spondyloarthropathies, polymyalgia rheumatica, ankylosing spondylitis, Reiter's Syndrome, psoriatic arthropathy, enteropathic arthritis (related to inflammatory bowel disease, such as haemorrhagic colitis and Crohn's disease), neuropathic arthropathy, acute rheumatic fever, gout, chondrocalcinosis, calcium hydroxyapatite crystal deposition disease, Lyme disease and all other degenerative joint diseases.

Another aspect of the present invention is related to the use of the pharmaceutical composition for the manufacture of a medicament in the treatment and/or the prevention of these mentioned diseases and/or symptoms (pain) induced by these diseases, possibly combined with an anti-inflammatory effect useful for the treatment and/or the prevention of diseases or symptoms of inflammatory origin.

According to a preferred embodiment of the present invention the composition presents a preferred formulation, preferably being an injectable solution for delivering an efficient amount (therapeutic dose) of the active compound present in the composition to a mammal subject including a human patient, especially in the knees, the hips and the spine of the subject.

Preferably, this injectable solution comprises from about 0.1 mg to about 100 mg/kg preferably from about 1 mg to about 10 mg/kg of body weight of this proteoglycan and/or glycosaminoglycan, preferably in the form of a proteoglycan-based hydrogel and may comprise from about 0.1 mg to about 100 mg/kg of patient body weight preferably from about 0.1 mg to about 0.8 mg/kg of patient body weight of a (an anti-inflammatory compound being) compound activating the alpha-2-adrenergic receptor, preferably an alpha-2-adrenergic receptor agonist, more preferably from about 3 µg to about 1500 µg of said alpha-2-adrenergic receptor agonist, still more preferably from about 30 µg to about 500 µg and even from 50 µg to 350 µg, or about 150 µg (of said alpha-2 adrenergic receptor agonist).

The injectable solution is adequate for intra-articular administration (percutaneous injection) in a joint of a mammal subject, preferably of a human patient.

This formulation is also adequate for local administration (percutaneous injection in/or in the vicinity of an inflamed joint of a mammal subject, preferably of a human patient), local administration injection that does concern the epidermis, the muscle or any deep organs.

The present invention is related to the surprising discovery that this intraarticular administration to a mammal subject, particularly a human patient of this pharmaceutical composition results in an improvement of symptoms associated with osteoarticular diseases such as a relief of osteoarticular pain, an improvement of joint mobility and/or function, a decrease in articular accumulation of inflammatory liquid, a shortening of the time to onset of the therapeutic activity of the first component, an increase in the duration of action of the first component and a reduction of joint degeneration or its progress possibly induced by the above mentioned diseases or pathologies.

The invention is also directed to a method for a treatment and/or a prevention (prophylaxis) of a condition selected from the group consisting of the above mentioned diseases or symptoms through an administration to a mammal subject, preferably a human patient of a sufficient amount of the pharmaceutical composition of the invention, through an intra-articular administration, particularly in the knees, the hips and the spine of the mammal subject; preferably the human patient.

A combined intra-articular administration of hyaluronic acid and an alpha 2 adrenergic receptor agonist allows for a shorter onset of action, a longer duration of action, for a superior or at least equivalent efficacy and/or a possible decrease of side-effects associated with hyaluronic acid and with administration of alpha 2 adrenergic receptor agonists.

The composition and method of the present invention also allows a decrease of the number of required administrations to obtain a desired efficacy and allows for a faster onset of action.

A last aspect of the present invention is related to a kit of parts comprising one or more vials with the elements (carrier/diluent, glycosaminoglycan, 2-2-adrenergic receptor compound, anti-inflammatory agent, stem cells or a combination thereof) of the composition of the invention and a device for delivering this composition to an inflamed joint of a mammal subject preferably a human patient suffering from the above mentioned osteoarticular diseases or symptoms (pain) and having reservoir means for storing this pharmaceutical composition, piston means movable along the longitudinal axis of the reservoir for dispensing this pharmaceutical composition and, a hollow needle mounted on said reservoir means for delivering this pharmaceutical composition to the peripheral nerve of the mammal subject.

These and other objects and features of the invention will become more fully apparent when the following detailed description of the invention is read in conjunction with the accompanying examples and figures.

BRIEF DESCRIPTION OF THE FIGURES AND TABLES

FIG. 1 shows the VAS scale assessing pain from 0 "no pain at all" to 100 "maximum pain" after 3 intraarticular administration of clonidine 150 µg and hyaluronic acid at day 0, day 7 and day 14 in 2 patients suffering from gonarthritis.

FIG. 2 shows the WOMAC score assessing pain and function of the knee after 3 intra-articular administration of clonidine 150 µg and hyaluronic acid at day 0, day 7 and day 14 in 2 patients suffering from gonarthritis (worse situation=96).

FIG. 3 shows the Lequesne score assessing algofunctional score of the knee after 3 intra-articular administration of clonidine 150 µg and hyaluronic acid at day 0, day 7 and day 14 in 2 patients suffering from gonarthrosis (worse situation=24).

FIG. 4 shows the VAS scale assessing pain from 0 "no pain at all" to 100 "maximum pain" after one intra-articular administration of clonidine 150 µg and hyaluronic acid at day 0 in 1 patient suffering from coxarthrosis.

DETAILED DESCRIPTION OF THE INVENTION

Figure 1:
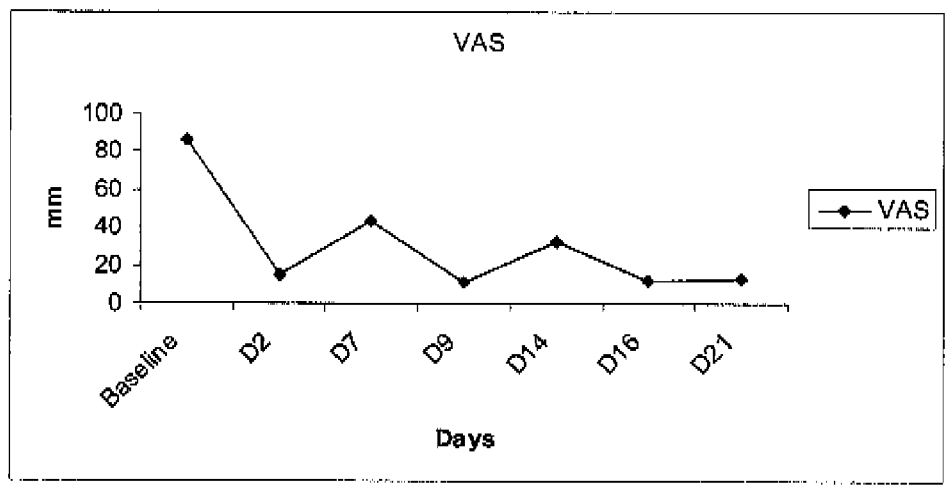

The term "intra-articular" as used herein refers to a percutaneous injection of a joint with the pharmaceutical composition of the invention.

The term "local administration" as used herein refers to a percutaneous injection in or in the vicinity of an inflamed joint. Local administration injection thus concerns the epidermis, the dermis, the muscle, or any deep organ.

The main advantages to local administration are to selectively restrict the analgesic and other effects to the injured areas. Furthermore, the local administration allows for high local concentration levels with little or no systemic release. The local administration and the intra-articular injection of hyaluronic acid is a recognised treatment of the above mentioned conditions.

The local administration and the intra-articular injection of alpha 2 adrenergic agonists are easily realizable and provide long lasting effect in combination with proteoglycans. In consequence, the problems related to placement of an invasive drug delivery system and the problems of bothersome side-effects, due to systemic release, can be strongly minimized. Health-related quality of life, patient satisfaction and economic assessment might be improved with such a treatment, especially in chronic conditions.

Preferably, the administrated compound is selected from the group consisting of a glycosaminoglycan, for example hyaluronic acid or a salt thereof or an ester of hyaluronic acid with an alcohol of the aliphatic, heterocyclic or cycloaliphatic series, or a sulphated form of hyaluronic acid or combination of agents containing hyaluronic acid. Suitable dosages of a proteoglycan-based hydrogel or a glycosaminoglycan or a derivative thereof will typically be from about 0.1 mg to about 100 mg/kg body weight per day or from about 0.5 mg to about 10 mg/kg body weight per day more preferably from about 2 mg to about 8 mg by body weight per day and suitable dosage amounts for alpha 2 adrenergic receptor agonists.

In a preferred embodiment, the alpha 2 adrenergic receptor agonist may be clonidine, p-aminoclonidine, tiamenidine, 5-bromo-6-(2 imidazolidine-2-ylamino) quinoxaline, dexmedetomidine, detomidine, medetomidine, oxymetazonline, tizanidine, mivazerol, lofexidine, xylazine, guanfacine, guanclofine, guanoxabenz, or a derivative or structural analogue thereof, alpha-methyinorepherine, azepexole, indoramin, 6-allyl-2-amino-5,6,7,8-tetrahydro4H-thiazolo [4,5-d] azepine diHCl or a compound selected from the table 1 and analogs thereof.

TABLE 1

Classification of the alpha-2-adrenergic receptor agonists guanidines agmatine
betanidine
biguanides
cimetidine
creatine
gabexate
guanethidine
guanfacine
guanidine
impromidine
iodo-3 benzylguanidine
methylguanidine
mitoguazone
nitrosoguanidines
pinacidil
robenidine
sulfaguanidine
zanamivir
imidazoles 4-(3-butoxy-4-methoxybenzyl)imidazolidin-2-one
urocanic acid
amino-imidazole carboxamide
antazoline
biotine
bis (4-methyl-l-homo piperazinylthiocarbonyl)disulfide
carbimazole
cimetidine
clotrimazole
creatinine
dacarbazine
dexmedetomidine
econazole
enoximone
ethymizol
etomidate
fadrozole
fluspirilene
histamine
histidinol
idazoxan
imidazolidines imidazolines
clonidine
tolazoline
impromidine
levamisole
losartane
medetomidine
miconazole
naphazoline
niridazole
nitroimidazoles
ondansetron
oxymetazoline
phentolamine
tetramisole
thiamazole
trimetaphan
Derivatives of clonidine 2,6-dimethylclonidine
4-azidoclonidine
4-carboxyclonidine-methyl 3,5-dichlorotyrosine
4-hydroxyclonidine
4-iodoclonidine
alinidine
apraclonidine
chlorethylclonidine
clonidine 4-isothiocyanate
clonidine 4-methylisothiocyanate TABLE 1-continued Classification of the alpha-2-adrenergic receptor agonists clonidine receptor
clonidine-displacing substance
hydroxyphenacetyl aminoclonidine
N,N'-dimethylclonidine The active compounds used in accordance with the invention are known. Pharmaceutical preparations containing hyaluronic acid are commercially available as are clonidine and other alpha 2 adrenergic receptor agonists. The compounds can be manufactured in a known manner essentially in accordance with the processes described in the prior art.

The term "clonidine" as used, herein refers to N-(2,6-dichlorophenyl)-4,5-dihydro-1H-imidazol-2-amine and includes the pharmaceutically acceptable salts thereof, e.g., salts with inorganic acids, such as hydrohalic acids, or with organic acids, for example lower aliphatic monocarboxylic or dicarboxylic acids such as acetic acid, fumaric acid or tartaric acid or aromatic carboxylic acids such as salicylic acid are also suitable.

Clonidine is employed in a therapeutically effective amount. The present invention also encompasses the use of alpha 2 adrenergic receptor agonist for the manufacture of injectable formulations for a delivery to a joint or a close region thereof, a therapeutic dose of said agonist by intra-articular injection, wherein said solution comprises from about 3 µg to about 1500 µg of said alpha-2-adrenergic receptor agonist. Preferably, said formulation comprises from about 30 µg to about 500 µg of said alpha-2-adrenergic receptor agonist. More preferably said solution comprises from 50 µg to 350 µg of said alpha-2 adrenergic receptor agonist. In a preferred embodiment, the alpha 2 adrenergic receptor agonist is clonidine. The actual concentration of clonidine may vary, depending on the nature and degree of the pain syndromes being treated and whether the drug is being administered for therapeutic or prophylactic purposes.

Due to their anti-inflammatory properties, inhibition of pro-inflammatory cytokines TNF-alpha and IL1-beta and the increase of anti-inflammatory cytokines, such as TGF beta, alpha 2 receptor agonists in injectable administration will have applications in osteoarticular inflammatory conditions and in diseases where there are osteoarticular inflammatory conditions, such as those above mentioned.

According to the method and the formulation of the invention, an injection of the combination of hyaluronic acid and an alpha 2 adrenergic receptor agonist form induces a long lasting pain relief, both in human case and in an animal model of osteoarticular pain. The method is safe, devoid of major drug's side effects and allows for acute as well as chronic treatment and or prophylaxis without the use of too invasive technique.

Pharmaceutical carriers or adjuvant such as preservatives may be incorporated in an amount effective for inhibiting growth of microbes, such as bacteria, yeast and molds, in the composition. Any conventional preservative against microbial contamination of the product can be employed so long as it is pharmaceutically acceptable and is unreactive with clonidine. Preferred preservatives are antimicrobial aromatic alcohols, such as benzyl alcohol, phenoxyethanol, phenethyl alcohol, and the like, and esters of parahydroxybenzoic acid commonly referred to as paraben compounds, such as methyl, ethyl, propyl, and butyl esters of parahydroxybenzoic acid and the like and mixtures thereof, but are not limited thereto. Particularly preferred are benzyl alcohol and phenoxyethanol.

Optionally, anaesthetic agent, such as lidocaine and the like, can be included. For administration according to the invention the active quantities of the compounds that alleviate neuropathic pain can be contained together with customary pharmaceutical excipients and/or additives in solid or liquid pharmaceutical formulations.

Liquid, preparations such as solutions, suspensions or emulsions of the active ingredients, prepared by dissolving or dispersing the compounds, can contain the usual diluents such as water, oil and/or suspending aids such as polyethylene glycols and optional pharmaceutical adjuvants, in a carrier, such as, for example, aqueous saline, aqueous dextrose, glycerol, or ethanol, to form a solution or suspension and such like. Further additives such as preservatives, flavouring agents and such like may also be added.

EXAMPLES

Example 1

Four patients suffering from gonarthritis with knee effusion were administered one intraarticular injection of about 20 mg of hyaluronic acid and about 150 µg of clonidine in the injured knee. A second and a third intra-articular injections were realized 7 and 14 days later. Before each injection, the intra-articular liquid was removed and measured. Pain and mobility were evaluated at baseline (day 0), 48-72 hours after the intra-articular injections, before the next injection (day 7 and day 14) and at day 21. The evaluations consisted in a 0-100 mm visual analogue scale filled in by the patient recording pain intensity (0=no pain, 100=intolerable pain), the WOMAC score (worse possible score=96) recording pain and mobility and an algofunctional scale (Lequesne Index, worse score=24).

Figure 2:
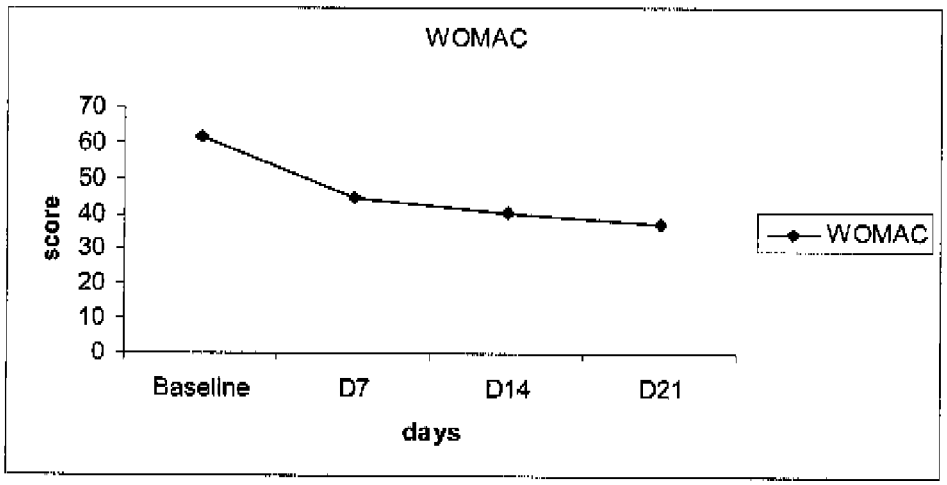
Figure 3:
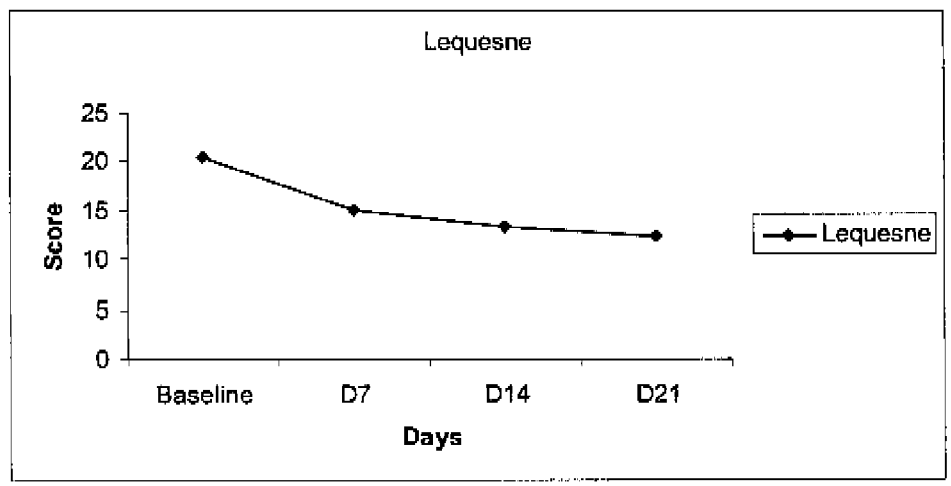

As shown in FIGS. 1, 2 and 3, the intra-articular administration of the combination induced unexpectedly an relief in pain (decrease in VAS from 86.5 mm to 14.5 mm) in 48 hours and the 2 re-administrations induced further improvements (VAS score=11 at day 9, 12 at day 16). This unexpected effect by comparison to the effect of either product was maintained for at least 1 week after the $3^{rd}$ injection as VAS score was 13 at day 21. Same results were obtained using the WOMAC score which additionally evaluated mobility of the injured knee. The WOMAC score decreased from 61 at baseline to 44, 41 and 37 at days 7, 14 and 21. Likewise the algofunctional score evaluated using the Lequesne scale showed a dramatic improvement with scores decreasing from 20 at baseline to 15, 13, and 12 respectively at day 7, 14 and 21. These results were totally unexpected as hyaluronic acid has not been shown to decrease pain score by more than 15 mm in meta-analyses that reassessed its efficacy and the effects of hyaluronic acid do not occur before 3 to 4 weeks. No data are available for clonidine in osteoarthritis.

Example 2

To two patients suffering from coxarthritis, was administered a single intra-articular injection of about 20 mg of hyaluronic acid and about 150 µg of clonidine in the injured hip. Pain and mobility were evaluated at baseline (day 0), and at day 7, day 14, day 21 and day 28. The evaluations consisted in a 0-100 mm visual analog scale filled in by the patient recording pain intensity (0=no pain, 100=intolerable pain), the WOMAC score (worse possible score=96) recording pain and mobility and an algofunctional scale (Lequesne, worse score=24).

Figure 4:
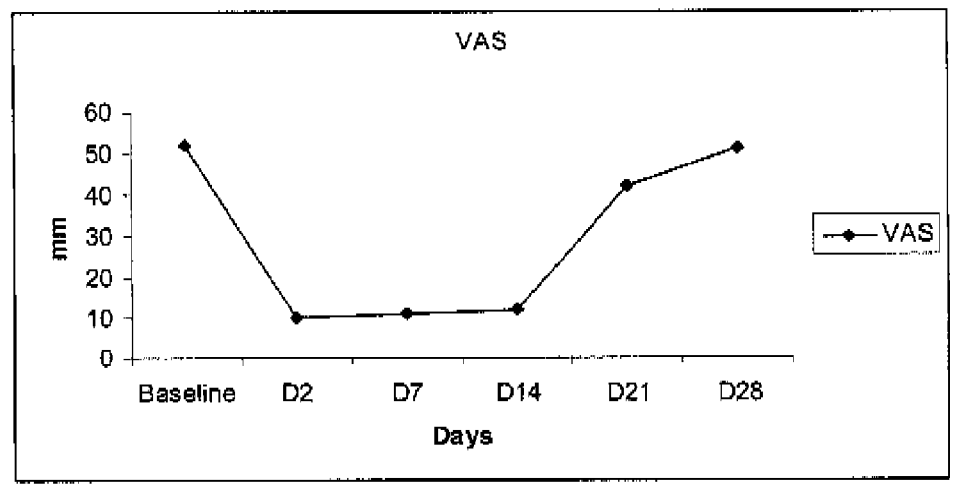
Figure 5:
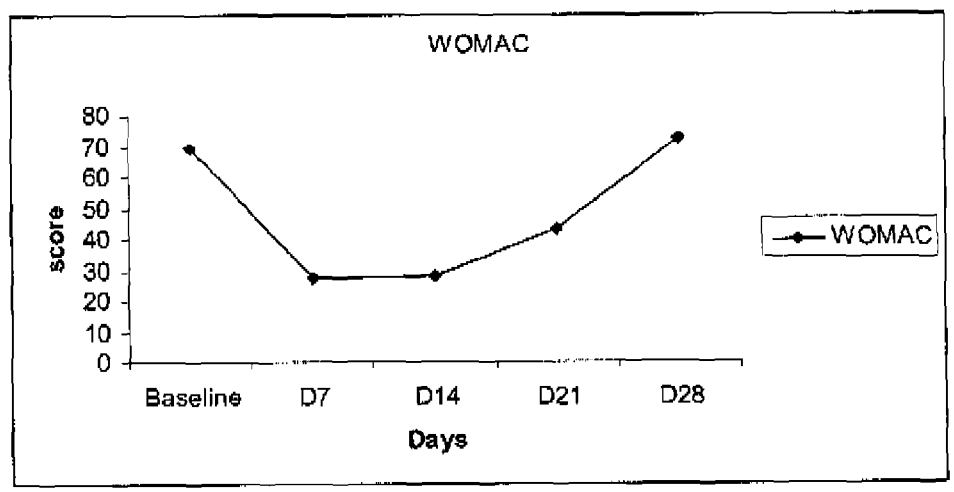
FIG. 5 shows the WOMAC score assessing pain and function of the hip after one intraarticular administration of clonidine 150 µg and hyaluronic acid at day 0 in 1 patient suffering from coxarthrosis.
Figure 6:
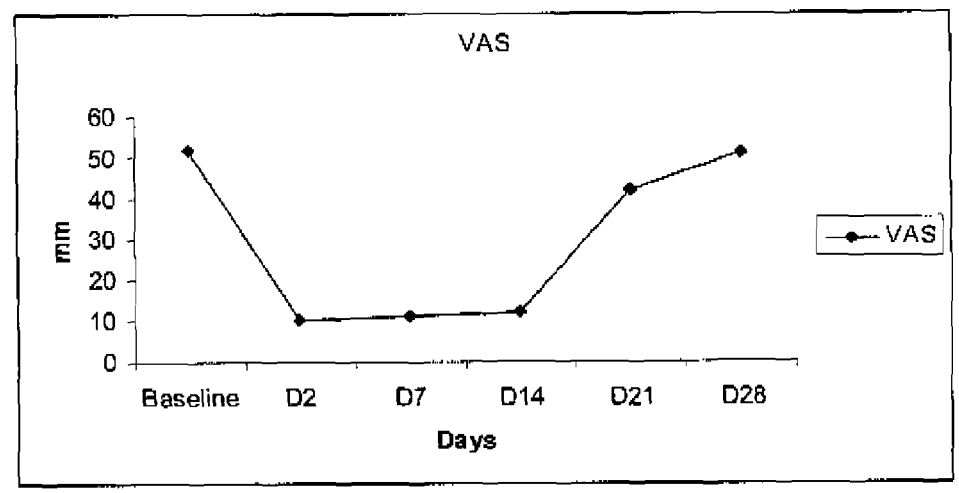
FIG. 6 shows the Lequesne score assessing pain and function of the hip after one intra-articular administration of clonidine 150 µg and hyaluronic acid at day 0 in 1 patient suffering from coxarthrosis.

In patients with coxarthritis who were treated with this combination, the effect of a single intra-articular injection of about 20 mg of hyaluronic acid and about 150 µg of clonidine induced an immediate, marked, and prolonged effect as shown in FIGS. 4, 5, and 6. VAS decreased from 52 mm at baseline to 10, 11, 42 and 51 at days 7, 14, 21 and 28. Likewise, the WOMAC score decreased from 69 at baseline to 27, 28, 43 and 72 at days 7, 14, 21 and 28 respectively and the algofunctional score from 13 to 8 and 8 at days 7 and 14 and returned to pre injection values at days 21 and 28: (13 and 14 respectively).

These results were unexpected as there is no reports of such improvement in the 3 weeks following the administration of hyaluronic acid. No data are available with clonidine. The prolonged antalgic effect was also totally unexpected.

In summary, patients treated by simultaneous intra-articular injection of clonidine and of hyaluronic, showed a dramatic improvement of pain score (80%) and of joint functional score (60%); improvements which were maintained for ~2-3 weeks.

Similar favourable evolution was observed for swelling, which appeared to be significantly reduced. In this feasibility study, no major side-effects have been reported. Interestingly, only partial treatment escape was observed.

Example 3: Clinical Experience with Intra-articular Products

The most comprehensive clinical data have been reported for intra-articular (i) corticosteroids, (ii) hyaluronic acid and (iii) TNFCC inhibitors.

In a recent paper, Uthman et al. (Postgrad Med J, 2003 August; 79(934):449-53) reviewed all published data with intra-articular products. Besides corticosteroids and hyaluronic acid, only anecdotic reports have been published on substances or approaches as diverse as orgotein, radiation synovectomy, dextrose prolotherapy, silicone, saline lavage, saline injection without lavage, analgesic agents, glucosamine, somatostatin, sodium pentosan polysulfate, chloroquine, mucopolysaccharide polysulfuric acid ester, lactic acid solution, and thiotepa cytostatics, without conclusive evidence of efficacy.

Example 4: Comparison of Clonidine/Hyaluronic Acid with Intra-articular Anti-Inflammatory Treatments A (historical/published data) comparison of standard mono-arthritis treatments with the combination clonidine-hyaluronic acid tends to favour this combination for the efficacy on mono-arthritis symptoms.

The efficacy is measured by a reduction in score value (which demonstrates an improvement), such as pain scores or functional scores.

|  | Reduction in Pain | Improvement in Function | Reduction in Swelling | Side-Effects** |
|---|---|---|---|---|
| $A_2A$/HA | −85% | −55% | +++ | None |
| Corticosteroids* | −30% | −30% | +++ | 5% |

-continued

|  | Reduction in Pain | Improvement in Function | Reduction in Swelling | Side-Effects** |
|---|---|---|---|---|
| Hyaluronic acid* | −10% | −15% | n.r. | None |
| TNFα inhibitors* | −30% | n.r. | ++ | None | n.r. = not reported,
n.m. = not measured;
*average data from available meta-analyses and/or published studies (Bliddal et al, 2006, Bliddal et al 2006, Fernandez Lopez and Ruano-Ravina, 2006, Arrich et al., 2005; Bellamy et al. 2006; Bellamy et al. 2006);
**major side effects only

Example 5: Comparison of A2A/HA with Intra-Articular HAs

|  | Reduction in Pain | Reduction in Pain (max effect reported) | Improvement in Function | Reduction in Swelling |
|---|---|---|---|---|
| A$_2$A/HA Hyaluronic Acid | −85% | — | −55% | +++ |
| Arich et al., 2005 | 0% | −17% | −11% | n.r. |
| Wang et al., 2004 | −8% | −24% | n.r. | n.r. |
| Kolarz et al., 2003 | −55% | — | −23% | n.r. |
| Lo et al., 2004 | −7% | −47% | n.r. | n.r. |

The maximal hyaluronic acid, effects reported in literature is a 55% improvement in pain and a 23% in function (Kolarz et al. 2003), but these effects seem, to have never been replicated (Arich et al., 2005; Wang et al., 2004; Lo et al., 2003).

These maximum hyaluronic acid effects are significantly below the effects reported with the combination clonidine-hyaluronic acid (on pain 55% vs 85% as well, as function 23% vs 55%, respectively). There is no reported benefit on swelling with hyaluronic acid, a major pain component in osteoarthritis and other inflammatory joint disorders, while there is a strong reduction in swelling with the combination clonidine and hyaluronic acid.

The effect of clonidine has never been studied in chronic knee pain before.

The effects of clonidine in acute pain studies have been show not to exceed 72 hours (Gentili et al, 2001), with even a minimum effect duration of 4 hours (Alagol et al, 2005), while the combination clonidine-hyaluronic acid has been shown to have an effects of up to 2 weeks.

Example 6

The effects of clonidine above were extrapolated to other alpha-2-adrenergic agents.

The inhibition of IL-1beta release by alpha-2-adrenergic agonists, induced by LPS stimulation of TH1 cells, is measured under control conditions (dexamethasone).

The results of the study are:
Dexamethasone $10^{-7}$ M inhibits ~65% of IL-1 beta secretion by LPS-stimulated TH1 cells
Mivazerol and clonidine, at $10^{-7}$ M and $10^{-5}$ M, display 80-90% of DEX ($10^{-7}$ M) efficacy
Guanfacine and moxonidine are at 40 to 60% of DEX effect, while others have only marginal effects
Guanabenz, Brimonidine and Methyldopa have no effects

Example 7

The effects of the combination clonidine and hyaluronic acid were tested in a model of Peripheral Blood Mononuclear Cells. In brief, PBMCs (Peripheral blood mononuclear cells) from heparinized venous blood of healthy volunteers were isolated by Ficoll-gradient centrifugation. MNC (Mononuclear cells) were washed three times in PBS and resuspended in RPMI-1640 medium supplemented with 100 U/mL penicillin, 100 µg/mL streptomycin, and 10% heat-inactivated FBS. Cells were seeded at 100.000 cells in 96-well plate in a total volume of 200 µL/well.

PBMC, at 100.000 cells/200 µL, were plated in 96-well microtiter plates and stimulated or not 10 µg/mL phytohemagglutinin (PHA). Effects of hyaluronic acid "HA" (200 µg/mL) and p-aminoclonidine "A2A" (5 µM) were tested on PBMC.

Proliferation Assay. The culture was incubated with 1 µCi/mL 3H-thymidine for 24 h before end of culture to measure the proliferation. Then, cells were washed twice with ice-cold PBS and twice with ice-cold 5% trichloroacetic acid (TCA). Finally, cells were lysed with 0. 1N NaOH-0.1% Triton-X100. Supernatants were collected and analyzed on a beta-counter in presence of scintillation liquid. Results were done in cpm ("count per minute"=disintegration number of radioactive element observed in series of successive counts of one minute).

IL-1beta detection (By ELISA). Levels of IL-1β from PBMC or culture supernatants were measured by Quantikine ELISA kit (R&D Systems Inc, Minneapolis, USA). The minimum detectable concentration of IL-1β was estimated at 1.0 pg/mL.

The release of IL-1beta by PBMC and the proliferation of PBMC, induced by PHA stimulation, were set as controls, and compared with the measures for PBMC treated with HA and/or A2A.

The inhibition of PBMC release of IL-1beta and the inhibition of PBMC proliferation, induced by LPS stimulation of TH1 cells, were also measured and provided similar trends as for PHA stimulated cells.

Effects of HA Alone

| Conditions tested | IL-1β detection (pg/mL) | Proliferation (cpm) |
|---|---|---|
| PBMC | ND* | 769 |
| PBMC + PHA | 2185 | 16069 |
| PBMC + HA | 2095 | 364 |
| PBMC + PHA + HA | 6394 | 9087 |

| Conditions tested | IL-1β detection (%) | Proliferation (%) |
|---|---|---|
| PBMC | ND* | 5 |
| PBMC + PHA | 100 | 100 |
| PBMC + HA | 96 | 2.2 |
| PBMC + PHA + HA | 293 | 57 |

IL-1beta secretion induced by PHA stimulation shows a significant increase over basal condition (where IL-1beta levels were undetectable) and was set at 100. Proliferation of PMBC cells also significantly increased, by a factor of about ~20. Surprisingly, a similar cytokine increase—over basal condition—was observed with addition of HA alone, while PBMC proliferation was not affected. When stimulated by PHA, the addition of HA synergistically increases IL-1beta secretion, 3 times over the stimulated conditions, but was able to reduce PBMC proliferation by a factor 2.

Effects of A2A Alone

| Conditions tested | IL-1β detection (pg/mL) | Proliferation (cpm) |
|---|---|---|
| PBMC | ND* | 769 |
| PBMC + A2A | ND* | 786 |
| PBMC + PHA | 2185 | 16069 |
| PBMC + PHA + A2A | ND* | 16212 |

| Conditions tested | IL-1β detection (%) | Proliferation (%) |
|---|---|---|
| PBMC | ND* | 5 |
| PBMC + A2A | ND* | 4.9 |
| PBMC + PHA | 100 | 100 |
| PBMC + PHA + A2A | ND* | 101 |

A2A has no effect on basal—unstimulated-conditions. Interestingly, when stimulated by PHA, the addition of A2A totally suppresses the increase in IL-1beta secretion due to PHA stimulation, to undetectable levels, but was not able to inhibit PBMC proliferation.

Effects of Combination of A2A & HA

| Conditions tested | IL-1β detection (pg/mL) | Proliferation (cpm) |
|---|---|---|
| PBMC + PHA | 2185 | 16069 |
| PBMC + PHA + HA | 6394 | 9087 |
| PBMC + PHA + HA + A2A | 3053 | 5445 |

| Conditions tested | IL-1β detection (%) | Proliferation (%) |
|---|---|---|
| PBMC + PHA | 100 | 100 |
| PBMC + PHA + HA | 292 | 56 |
| PBMC + PHA + HA + A2A | 139 | 34 |

Interestingly, the combination HA/A2A demonstrates a potent anti-inflammatory effect over the PHA/HA condition. Indeed, the addition of A2A was able to significantly revert—by over 50%—the increase in IL-1beta secretion due to PHA/HA stimulation, bringing its level to the one of the PHA alone condition. Surprisingly, A2A was further able to inhibit PBMC proliferation, by another 35%.

During inflammation, lower molecular weight fragments of hyaluronan are known to be inflammatory and immune-stimulatory agents by inducing the secretion of cytokines such as IL-6 and monocyte chemoattractant protein (MCP-1). HA has also the property to enhance the adhesion of lymphocytes and monocytes to the extracellular matrix (Yamawaki et al., 2009). These experiments show that hyaluronic acid has a potent stimulatory effect on cytokine (e.g., IL-1beta) production without PBMC proliferation.

It has been demonstrated that clonidine alters the Th1/Th2 cytokine production (Xu et al., 2007; Cook-Mills et al., 1998). These experiments show that the addition of alpha 2 adrenoreceptor agonists totally suppresses the increase in cytokine (e.g., IL-1beta) secretion due to PHA stimulation, but is not able to inhibit PBMC proliferation.

Surprisingly, the combination HA/A2A demonstrates a potent anti-inflammatory effect both on cytokine production and inflammatory cell proliferation. Indeed, the addition of A2A to HA was able to significantly inhibit the increase in IL-1beta secretion and was farther able to inhibit PBMC proliferation.

The invention claimed is:

1. A method for treating an osteoarticular disease in a mammalian subject, the method comprising intra-articularly injecting in a joint of the subject in need thereof a pharmaceutical composition comprising:
   an effective amount of hyaluronic acid or a derivative thereof; and
   an effective amount of α2 adrenergic receptor agonist compound, the α2 adrenergic receptor agonist compound comprising clonidine or p-aminoclonidine;
   wherein the pharmaceutical composition synergistically reduces joint degeneration by providing a decrease in articular accumulation of liquid and inflammation, synergistically reduces joint pain and/or synergistically improves joint mobility and function for two weeks or more.

2. The method of claim 1, comprising administering the pharmaceutical composition by intra-articular injection to the patient once a week.

3. The method of claim 1, comprising administering the pharmaceutical composition by intra-articular injection to the patient twice a week.

4. The method of claim 1, comprising administering the pharmaceutical composition by intra-articular injection to the patient once in two weeks or less.

5. The method of claim 1, wherein the pharmaceutical composition comprises from about 0.1 mg to about 100 mg of the hyaluronic acid or derivative thereof per kg of body weight of the subject and from about 0.1 μg to about 1 mg of the compound activating the α2adrenergic receptor.

6. The method of claim 1, wherein the intra-articular injection of the pharmaceutical composition reduces nociceptive pain associated with the osteoarticular disease.

7. The method of claim 1, wherein the osteoarticular disease is selected from the group consisting of osteoarthritis, degenerative arthritis, gonarthrosis, and coxarthrosis.

8. The method of claim 1, wherein the pharmaceutical composition further comprises human adult mesenchymal stem cells or non-human embryonic mesenchymal stem cells.

9. The method of claim 1, wherein the pharmaceutical composition further comprises a pharmaceutical carrier or diluent.

* * * * *